United States Patent [19]
Grusby et al.

[11] Patent Number: 5,866,760
[45] Date of Patent: Feb. 2, 1999

[54] STAT6 DEFICIENT TRANSGENIC MICE

[75] Inventors: Michael J. Grusby; Mark H. Kaplan, both of Boston, Mass.

[73] Assignee: President and Fellows of Harvard College, Cambridge, Mass.

[21] Appl. No.: 823,051

[22] Filed: Mar. 21, 1997

Related U.S. Application Data

[60] Provisional application No. 60/013,981 Mar. 22, 1996.
[51] Int. Cl. [6] .............................. C12N 5/00; C12N 15/00; C12N 15/09
[52] U.S. Cl. ............................ 800/18; 435/455; 435/462; 435/463; 435/325; 435/320.1; 435/92.1; 424/9.21
[58] Field of Search ....................... 800/2, 18; 435/172.3, 435/69.1, 325, 320.1, 92.1, 455, 462, 463; 424/9.21

[56] References Cited

PUBLICATIONS

Bradley et al., Biotechnology, vol. 10, pp 534–539, May 1992.
Seamark, Reprod. Fertil. Dev., vol. 6, pp. 653–657, 1994.
Mullins et al. Journal of Clinical Investigations, vol. 98. No. 11, pp S37–S40, 1996.
Capecchi, Scientific American, vol. 270, No. 3, pp. 34–41, Mar. 1994.
Hou et al. Science, vol. 265, pp. 1701–1706, Sep. 16, 1994.
Quelle et al., Molecular and Cellular Biology, vol. 15, No. 6, pp. 3336–3343, Jun. 1995.
Shimoda et al. (1996) Nature. vol. 380, 630–633.
Copies of pages from lab notebook (4p).
Keystone symposium agenda (6p).
St. Jude Children's Research Hospital interoffice memorandum (2p).

*Primary Examiner*—Jasmine C. Chambers
*Assistant Examiner*—Jill D. Martin
*Attorney, Agent, or Firm*—Richard Aron Osman

[57] ABSTRACT

The invention provides methods and compositions for evaluating modulators of the Stat6 signaling pathway; in a particular, transgenic mice comprising a transgene within a Stat6 allele locus, encoding a selectable marker and displacing the SH2-encoding domain of the Stat6 allele. More particularly, the transgene may comprise 3' and 5' regions with sufficient complementarity to the natural Stat6 allele at the locus to effect homologous recombination of the transgene with the Stat6 allele. Such mice provide useful animal models for determining the effect of candidate drugs on a host deficient in Stat6 function. The invention provides a variety of methods for making and using the subject compositions; in particular, methods for determining the effect of a candidate drug on a mouse deficient in Stat6 function and methods of evaluating the side effects of a Stat6 function inhibitor.

2 Claims, 1 Drawing Sheet

STAT6 DEFICIENT TRANSGENIC MICE

This is a provisional Application Ser. No. 60/013,981 filed Mar. 22, 1996.

FIELD OF THE INVENTION

The field of the invention is transgenic animals with a disrupted Stat6 allele.

BACKGROUND

Signal transducers and activators of transcription (Stat) proteins are a recently identified class of transcription factors responsible for mediating may cytokine-induced responses. These proteins exist in a latent form in the cytoplasm and become phosphorylated by the Janus kinase (JAK) family of tyrosine kinases following cytokine-receptor interactions. Once phosphorylated, Stat proteins dimerize, translocate to the nucleus, and bind to specific DNA sequences to regulate gene transcription (Ihle, 1995; Schindler and Darnell, 1995). Of the presently know Stat proteins, only Stat6 is activated in response to the cytokine interleukin-4 (IL-4) (Kotanides and Reich, 1993; Hou et al, 1994; Schindler et al, 1994; Quelle et al., 1995). IL-4 is secreted by several cell types including stimulated T lymphocytes, mast cells, and basophils (Howard et al., 1982; Lee et al, 1986; Paul and Ohara, 1987; Yoshimoto and Paul, 1994; Sad et al., 1995). While initially identified by its ability to support the growth and differentiation of B lymphocytes costimulated with submitogenic doses of anti-immunoglobulin (Howard et al., 1982), IL-4 is now known to have pleiotropic effects on the immune system. IL-4 is essential for the induction of immunoglobulin E (IgE) synthesis by activated B lymphocytes and influences class switching to IgG1 as well (Vitetta et al, 1985; Coffman et al., 1986). B cells stimulated with IL-4 increase their cell surface expression of major histocompatibility complex (MHC) class II molecules (Noelle et al., 1984), IL-4 receptor (IL-4R) (Ohara and Paul, 1988), and the low affinity IgE receptor CD23 (Conrad et al., 1987). IL-4 also induces the proliferation of T lymphocytes and is important for the differentiation of T helper 2 (Th2) cells (Le Gros et al., 1990; Swain et al., 1990). Indeed, the analysis of IL-4-deficient mice generated by gene targeting in embryonic stem (ES) cells has confirmed the importance of this cytokine in mediating many of these responses (Kuhn et al., 1991; Kopf et al., 1993).

IL-4-induced responses result from the interaction of ligand with a cell surface receptor composed of a cytokine-specific a chain and the common gc chain also used by IL-2 (Takeshita et al., 1992). IL-7 (Nognchi et al, 1993; Kondo et al, 1994), IL-9 (Russell et al., 1994) and IL-15 (Giri et al., 1994) receptors. Recent studies have shown that the a chain of the IL-4R is also a component of the high affinity IL-13 receptor (Lin et al., 1995; Zurawski et al, 1995; Hilton et al., 1996). Engagement of the IL-4R leads to the activation of at least two distinct signaling pathways. One involves the activation of Stat6 through phosphorylation by Jak1 and Jak 3 (Johnston et al., 1994; Witthuhn et al., 1994). The Stat pathway is thought to be important because the promoters of several genes know to be regulated by IL-4 contain the consensus Stat6-binding site TTCN4GAA (Schindler et al., 1995), and fragments of promoters of Ie and other genes containing this sequence bind Stat6 present in extracts from cells stimulated with IL-4 (Ichiki et al., 1993; Kotanides and Reich, 1993; Schindler et al., 1994). In addition to Stat6 activation, stimulation of the IL-4R has also been shown to induce the phosphorylation of an insulin receptor substrate (IRS) termed 4PS or IRS-2 (Keegan et al., 1994; Sun et al., 1995). Activated IRS-2 associates with phosphatidylinositol 3-kinase and may be responsible for certain IL-4-induced responses. For example, cell lines transfected with an IL-4R mutant that in incapable of inducing the tyrosine phosphorylation of IRS-2 have an impaired ability to proliferate in response to IL-4 (Keegan et al., 1994).

SUMMARY OF THE INVENTION

The invention provides methods and compositions for evaluating modulators of the Stat6 signaling pathway. For example, the invention provides transgenic non-human mammals having at least one structurally and functionally disrupted Stat6 allele. In particular embodiments, the mammals are mice comprising a transgene within a Stat6 allele locus, encoding a selectable marker and displacing the SH2-encoding domain of the Stat6 allele. More particularly, the transgene may comprise 3' and 5' regions with sufficient complementarity to the natural Stat6 allele at the locus to effect homologous recombination of the transgene with the Stat6 allele. Such mammals provide useful animal models for determining the effect of candidate drugs on a host deficient in Stat6 function.

The invention provides a variety of methods for making and using the subject compositions. For example, the invention provides methods for determining the effect of a candidate drug on a host deficient in Stat6 function, such as: contacting a transgenic mouse having at least one disrupted Stat6 allele with a candidate drug; and, detecting the presence or absence of a physiological change in the mouse in response to the contacting step. The invention also provides methods of evaluating the side effects of a Stat6 function inhibitor, such as: contacting a transgenic mouse having at least one disrupted Stat6 allele with a candidate drug; detecting the presence or absence of a physiological change in the mouse in response to the contacting step, wherein the presence of a physiological change indicates the inhibitor has side effects beyond Stat6 function inhibition.

DETAILED DESCRIPTION OF SPECIFIC EMBODIMENTS OF THE INVENTION

Figure 1:
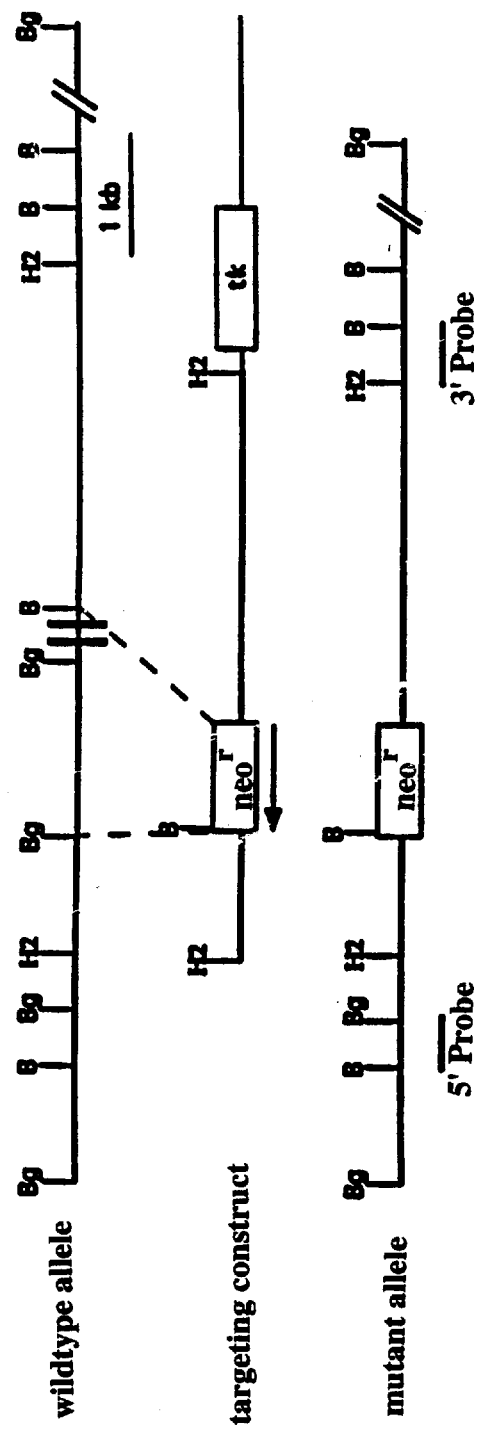
FIG. 1 shows a schematic of the targeting construct used to disrupt the Stat6 gene.

The following description is offered by way of illustration and not by way of limitation.
Generation of Stat6-Deficient Mice A gene-targeting construct was generated that replaces exons encoding amino acids 505–584 of Stat6 with a cassette containing the neomycin resistance gene (FIG. 1). In the Figure, the two exons of the Stat6 gene that were replaced with the neomycin resistance gene are indicated as closed bars. 5' and 3' probes used to verify correctly targeted clones are indicated under the mutant allele. Retriction enzymes are the following: B, BamHI;

Bg, BgII; H2, HindII. The targeted region of the Stat6 gene encodes the SH2 domain required for Stat dimerization, thereby insuring that any mutant protein that may be made from the targeted locus will not be functional. The targeting construct was electroporated into D3 ES cells, and Southern (DNA) analysis of G418-resistant clones revealed that 6 to 60 clones had undergone homologous recombination at the Stat6 locus. Correctly targeted clones were injected into BALC/c blastocysts to generate chimeras.

Once the disrupted Stat6 allele was transmitted through the germline, heterozygotes were intercrossed to generate mice homozygous for the Stat6 mutation. Despite the widespread expression of Stat6 transcripts in adult tissues (Hou et al., 1994), Stat6$^{-/-}$ mice are grossly indistinguishable from their control littermates. Inmunoblot analysis of cell lysates from both spleen and thymus confirmed that Stat6$^{-/-}$ mice do not express Stat6 protein. All lymphocyte subsets in the thymus and peripheral lymphoid organs of Stat6$^{-/-}$ mice appear to be represented normally when analyzed by flow cytometry for CD3, CD4, CD8, and B220.

Stat6 Is Required for IL-4-Induced Increases in the Expression of Cell Surface Markers Several cell surface molecules, including MHC class II antigens and the IL-4R are know to be up-regulated on lymphocytes in response to IL-4 (Noelle et al., 1984; Ohara and Paul, 1988). To examine the role of Stat6 in the regulation of IL-4-inducible genes, lymph node cells from control or Stat6$^{-/-}$ mice were incubated for 18 hr in 1,000 U/ml IL-4 and then examined by flow cytometry. B cells from control mice show a striking increase in their cell surface expression of MHC class II molecules in response to stimulation with IL-4, while both B and T cells demonstrate an increase in the expression of IL-4R. In contrast, no induction of these genes is seen in lymphocytes from Stat6$^{-/-}$ mice in response to IL-4. The basal level of expression of these genes on lymphocytes from control and Stat6$^{-/-}$ mice is similar, and lipopolysaccharide stimulation of B lymphocytes from Stat6$^{-/-}$ mice and their control littermates leads to an equivalent up-regulation in the cell surface expression of MHC class II antigens. These results demonstrate that Stat6 is required for the IL-4 -induced increase in expression of genes regulated by this cytokine.

Lymphocytes From Stat6$^{-/-}$ Mice Have a Greatly Impaired Proliferative Response to IL-4

As mentioned above, cell lines transfected with an IL-4R mutant that is incapable of inducing the tyrosine phosphorylation of IRS-2 have an impaired ability to proliferate in response to IL-4 (Keegan et al., 1994). Similar transfectants containing a truncated IL-4R incapable of mediating the tyrosine phosphorylation of Stat6 retain their mitogenic response to IL-4 (Keegan et al., 1994; Quelle et al., 1995). These results suggested that the IRS-2 signaling pathway, rather than the Stat6 pathway, is important for the proliferative response to IL-4. to examine more definitively the role of Stat6 in mediating the proliferation of lymphocytes in response to IL-4, lymph node cells from Stat6$^{-/-}$ mice and control littermates were stimulated for 48 hr in the presence of graded doses of IL-4 and subsequently assayed for [3H] thymidine incorporation. The proliferative response of lymphocytes from Stat6$^{-/-}$ mice is almost completely abrogated. In contract with lymphocytes from control mice, which show a 40-fold increase in proliferation in response to 1,000 U/ml IL-4, the proliferative response of lymphocytes from Stat6$^{-/-}$ mice is only 4- to 5-fold over background at this concentration of IL-4 and undetectable at 100 U/ml I1-4. No differences were observed in the proliferation of lymphocytes from Stat6$^{-/-}$ mice or control littermates to graded doses of IL-2, whose receptor uses the same γc chain as IL-4, or in their proliferation in response to either anti-CD3 or lipopolysaccharide.

It is noteworthy that the ability of mutant forms of the IL-4R both to induce the phosphorylation of signaling molecules and to generate of proliferative response was assayed using transfectants of a myeloid progenitor cell line (Keegan et al., 1994; Quelle et al., 1995). Therefore, the apparently greater importance of IRS-2 in mediating prolif-erative signals in myeloid cells in response to IL-4 may reflect differences in the cell types examined. However, these results do not preclude a role for IRS-2 in mediating the proliferative signal in lymphocytes. Indeed, the small amount of proliferation of Stat6$^{-/-}$ lymphocytes to high concentrations of IL-4 may be due to signals generated through other pathways, such as that involving IRS-2. Additionally, our data do not rule out the possibility that the reduced proliferation of Stat6$^{-/-}$ lymphocytes in response to IL-4 results from the inability of IL-4 to induce the up-regulation of IL-4R and amplify the proliferative response. Nevertheless, the data demonstrate that a normal IL-4-induced proliferative response in lymphocytes is dependent on Stat6 and that Stat proteins are involved in transformation and cell growth (Danial et al., 1995; Migone et al., 1995; Yu et al, 1995).

Stat6 Is Required for the Generation of an IgE Response

IL-4 has been demonstrated to be essential for the generation of IgE in response to a number of antigenic challenges, including immunization with anti-IgD (Conrad et al., 1990; Finkelman et al., 1991). To analyze the role of Stat6 in this IL-4-mediated response, Stat6$^{-/-}$ mice and control littermates were injected with IgD-specific monoclonal antibodies. All mice, regardless of their genotype, developed splenomegaly in response to immunization with anti-IgD. Sera were analyzed by enzyme-linked immunosorbent assay (ELISA) for the presence of all immunoglobulin isotypes both before immunization and 9 days postinjection with anti-IgD. The basal levels of IgM, IgG1 , and IgG2$a$ were similar between Stat6$^{-/-}$ mice and control littermates. Following immunization with anti-IgD, control mice show an increase in serum levels of each of these immunoglobulin isotypes and, consistent with previous reports, a striking induction in the level of IgE is evident. While sera from Stat6$^{-/-}$ mice immunized with anti-IgD show an increase in the levels of IgG1 and IgG2a similar to that seen in the sera of immunized control mice, Stat6$^{-/-}$ mice did not have detectable levels of IgE. The induction of IgG1 in Stat6$^{-/-}$ mice is not surprising, since IL-4-deficient mice also have detectable levels of IgG1 (Kuhn et al., 1991) and, we have noted, an increase in serum IgG1 following anti-IgD injection is seen in IL-4-deficient mice and therefore is not dependent on IL-4.

T Lymphocytes From Stat6$^{-/-}$ Mice Do Not Differentiate Into Th2 Cells

To address directly the role of Stat6 in the differentiation of Th cell subsets, spleen cells from control and Stat6$^{-/-}$ mice were stimulated in vitro with anti-CD3 and cultured in the presence of either IL-12 and anti-IL-4 to generate Th1 cells, or IL-4 and anti-interferon-γ (IEN$_{65}$) to generate to generate Th2 cells. After 1 week in culture, cells were washed, restimulated with anti-Cd3, and culture supernatants were assayed for the presence of various cytokines by ELISA. Th1 cell differentiation is unimpaired in Stat6$^{-/-}$ mice as evidenced by their ability to produce similiar amounts of IFNg and granulocyte/macrophage colony-stimulating factor compared with that produced bycontrol cells cultured under identical conditions. As expected, barely detectable levels of IL-4 and IL-5 are produced by cells cultured under Th1-inducing conditions irrespective of their genotype. When lymphocytes from control mice were cultured under conditions that favor the generation of Th2 cells and subsequently assayed for their ability to produce IL-4 and IL-5, they were found to secrete high levels of these cytokines. In contrast, lymphocytes from Stat6$^{-/-}$ mice demonstrated an inability to produce IL-4 and IL-5 when cultured under identical conditions. Thus, T lymphocytes from Stat6$^{-/-}$ mice are almost completely impaired in their ability to differentiate into Th2 cells, a result indicating that Stat6 is essential for mediating the differentiation signals induced by IL-4.

It is noteworthy that the impairment in Th2 development seen in Stat6$^{-/-}$ mice is more pronounced than that observed in IL-4-deficient mice. Despite the importance of IL-4 in mediating the differentiation of Th2 cells, the limited generation of these cells can be detected in IL-4-deficient mice in response to infection with Nippostrongylus brasiliensis (Kopf et al., 1993) and following in vitro differentiation. the more profound defect in Th2 development seen in Stat6$^{-/-}$ mice suggests that a cytokine other than IL-4 may be capable of inducing the differentiation of Th2 cells, but that, like IL-4, this cytokine generates differentiation signals through Stat6. IL-13 is one such candidate, since this cytokine shares many properties of the IL-4. Recent studies have shown that the α chain of the IL-4R is also involved in the formation of the high affinity IL-13 receptor (Lin et al., 1995; Zurawski et al., 1995; Hilton et al., 1996). Furthermore, while IL-13 does not induce T cell proliferation, IL-13 stimulation does lead to the tyrosine phosphorylation of Stat6.

To determine whether IL-13 is capable of inducing the differentiation of Th2 cells and, if so, whether this process is mediated by Stat6, spleen cells from control and Stat6$^{-/-}$ mice were stimulated in vitro with anti-CD3 and cultured in the presence of IL-13 and anti-IFN-γ. Lymphocytes from control mice stimulated in the presence of IL-13 developed into Th2 cells, as evidenced by their production of high levels of IL-4 and IL-5 following subsequent restimulation. In contrast, IL-13 was not capable of generating Th2 cells from Stat6$^{-/-}$ lymphocytes. These results demonstrate that IL-13 is indeed capable of inducing the differentiation of Th2 cells, and that Stat6 is essential for the differentiation signals generated by both IL-4 and IL-13 in T cells. Furthermore, the ability of IL-13 to drive the differentiation of Th2 cells may account for the presence of Th2 responses to IL-4-deficient mice.

Taken together, our results with Stat6$^{-/-}$ mice demonstrate a critical role for this transcription factor in mediating IL-4-induced responses in lymphocytes. Other signaling pathways, including that involving the tyrosine phosphorylation and activation of other Stats or IRS-2, clearly cannot compensate for Stat6.

Our results also indicate that Stat6 is required for mediating the differentiation signals leading to the development of Th2 cells in response to IL-4. Interestingly, the defect in Th2 development seen in Stat6$^{-/-}$ mice is more severe than that seen in IL-4-deficient mice. These results may be explained by the observation that, like IL-4, IL-13 is also capable of inducing the Stat6-dependent differentiation of Th2 cells. Stat6$^{-/-}$ mice will be useful in identifying genetic programs necessary for the development of Th2 cells.

Experimental Procedures: Stem Cells and Blastocyst Injections

A gene targeting construct containing approximately 1 kb of 5' flanking sequence and 3 kb of 3' flanking sequence of the Stat6 gene was generated. The targeting construct (20 mg) was electroporated into D3 ES cells using a Bio-Rad gene pulser set at 25 mF/350V. After 9 days of selection in 180 mg/ml G418 and 2 mM gancyclovir, drug-resistant clones were picked into 24-well plates and expanded in culture. Screening for correctly targeted clones was done by Southern (DNA) analysis and, once identified, they were injected into 3.5 day postcoital BALB/c blastocysts.

Immunoblot Analysis

Total cellular extracts were prepared as previously described (Quelle et al., 1995), except that following centrifugation, extracts were dialyzed against 1 XD (Dignam et al., 1983). Protein (20 mg) was separated on an 8% polyacrylamide gel, and electrophoretically transferred onto nitrocellulose. The filter was blocked in 10% dry milk in 1 × TBST for 14 hr and subsequently probed with antisera directed against recombinant Stat6 (Schindler et al., 1995) at a 1:100,000 dilution for 1 hr. Stat1 anti-serum was produced against the C-terminal 33aa (Schindler et al., 1995). Protein bands were detected by enhanced chemiluminescence (Amersham, Arlington Heights, Ill.).

Antibodies and Cytokines

Antibodies to CD3 (145-2C11) and fluorescin isothiocyanate- and phycoerythrin-conjugated antibodies to I-A$^d$, I-E$^d$, I-A$^b$, and B220 were purchased from Pharmingen (San Diego, California). Recombinant IL-4 and antibody specific for IL-4R were purchased from Genzyme (Cambridge, Mass.). A fluorescein isothiocyanate-conjugated goat anti-rat immunoglobulin was purchased from KPL (Gaithersburg, Md.) and used as a secondary reagent for the IL-4R antibody. Mouse monoclonal antibodies specific of IgD$^a$ and nti-IL4 (11 B11) antibody are described in Finkelman et al., 1991 and Paul et al., 1987, respectively. Anti-IFN-g was purified from supernatant of the SMG-1 hybridoma. Recombinant IL-2 was obtained from Boehringer-Mannheim (Indianapolis, Ind.). Recombinant IL-13 was purchased from R and D Systems (Minneapolis, Minn.).

Flow Cytometry

Single cell suspensions were made from the indicated tissues. Cells (1×10$^6$) were incubated on ice with 1 mg monoclonal antibody for 1 hr and washed before analysis on a Becton-Dickenson FACScan.

Proliferation Assays

Lymph node cells were plated at 5×10$^4$/round-bottomed microwell with dilutions of the indicated lymphokine in RPMI1640 (Mediatech, Herndon, Va.) supplemented with 10% fetal calf serum (Hyclone, Logan, UT), penicillin-streptomycin, sodium pyruvate, nonessential amino acids, L-glutamine, HEPES (all from Mediatech) and 5×10$^5$M 2-mercaptoethanol. Cells were pulsed with 1 mCi [$^3$H] thymidine (New England Nuclear, Boston, Mass.) for the last 18 hr of a 48 hr culture period. Spleen cells were incubated at 10$^5$/well for lipopolysaccharide and anti-CD3 stimulations.

In Vivo IgE Production

Mice were injected with 100 mg of two anti-allotypic anti-IgD monoclonals in 200 ml phosphate-buffered saline. Mice were bled by the tall vein to obtain preimmunization serum. At 9 days postinjection, mice were sacrificed and bled by cardiac puncture. Immunoglobulin isotypes were analyzed by ELISA as previously described (Markowitz et al., 1993).

In Vitro T Cell Differentiation

For in vitro differentiation assays, 2×10$^6$ spleen cells/ml were cultured in medium as above and stimulated with 1 mg/ml plate-bound anti-CD3 and incubated with 10 mg anti-IL-4 plus 100 U/ml IL-12 (Th1) or 10 mg/ml anti-IFNγ (th2). After activation (24 hr), we added 50 U/ml of IL-2 to all cultures and 1,000 U/ml IL-4 or 25 pg/ml IL-13 to Th2 cultures. Cultures were supplemented with fresh medium after 4 days, washed, and restimulated after 7 days with plate-bound anti-CD3 in the absence of any additional reagents. Supernatants were collected 24 hr later. Cytokine ELISAs were performed as previously described (Kuchroo et al., 1995).

REFERENCES

S Coffman, R. L. et al. (1986). J. Immunol. 136, 4538–4541;
    Conrad, D. H. et al. (1987). J. Immunol. 139, 2290–2296;

Conrad; D. H. et al. (1990). J. Exp. Med. 171, 1497–1508. Danial, N. N. et al. (1995). Science 269, 1875–1877; Dignam, J. D. et al. (1983). Nucl. Acids Res. 11, 1475–1489; Finkelnan, F. D. et al. (1991). J. Exp. Med. 174,1179–1188; Giri, J. G. et al. (1994). EMBO J. 13, 2822–2830; Hilton, D. J. et al. (1996). Proc. Natl. Acad. Sci. U.S.A. 93, 497–501; Hou, J. et al. (1994). Science 265, 1701–1706; Howard, M. et al. (1982). J. Exp. Med. 155, 914–923; Ichiki, T. et al. (1993). J. Immunol. 150, 5408–5417; Ihle, J. N. (1995). Nature 377, 591–594; Johnston, J. A. et al. (1994). Nature 370, 151–153; Keegan, A. D. et al. (1994); Cell 76, 811–820; Kondo, M. et al. (1994). Science 263, 1453–1454; Kopf, M. et al. (1993). Nature 362, 245–248; Kotanides, H. and Reich, N. C. (1993). Science 262, 1265–1267; Kuchroo, V. K. et al. (1995). Cell 80, 707–718; Kuhn, R. et al. (1991). Science 254, 707–710; Le Gros, G. et al. (1990). J. Exp. Med. 172, 921–929; Lee, F. et al. (1986). Proc. Natl. Acad. Sci. U.S.A. 83, 2061–2065; Lin, J.-X. et al. (1995). Immunity 2, 331–339; Markowitz, J. S. et al. (1993). J. Inmunol. 150, 1223–1233; Migone, T.-S. et al. (1995). Science 269, 79–81; Noelle, R. et al. (1984). Proc. Natl. Acad. Sci. U.S.A. 81, 6149–6153; Noguchi, M. et al. (1993). Science 262, 1877–1880; Ohara, J. and Paul. W. E. (1988). Proc. Natl. Acad. Sci. U.S.A. 85, 8221–8225; Paul, W. E. and Ohara, J. (1987). Annu. Rev. Immunol. 5,429–459; Quelle, F. W. et al. (1995). Mol. Cell. Biol. 15, 3336–3343; Russell, S. M. et al. (1994). Science 266, 1042–1045; Sad, S. and Mosmann, T. R. (1995). Immunity 2, 271–279;Schindler, C. and Darnell, J. E., Jr. (1995). Annu. Rev. Biochem. 64, 621–651; Schindler, C. et al. (1994). EMBO J. 13, 1350–1356; Schindler, U. et al. (1995). Immunity 2, 689–697; Sun, X. L. et al. (1995). Nature 377, 173–177; Swain, S. L. et al. (1990). J. Immunol. 145, 3796–3806; Takeshita, T. et al. (1992). Science 257, 379–382; Vitetta, E. S. et al. (1985). J. Exp. Med. 162, 1726–1732; Witthuhn, B. A. et al. (1994). Nature 370, 153–157; Yoshimoto, T. and Paul, W. E. (1994). J. Exp. Med. 179, 1285–1295; Yu, C.-L. et al. (1995). Science 269, 81–83; Zurawski, S. M. et al. (1995). J. Biol. Chem. 270, 13869–13878.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A transgenic mouse whose germ cells and somatic cells contain a homozygous disruption of the endogenous Stat6 gene, wherein the disruption comprises the insertion of a selectable marker sequence, and wherein the disrupted Stat6 gene results in no detectable expression of Stat6 in the cells of the mouse and a phenotype defined by impaired IL-4 induced lymphocyte expression of MHC class II molecules, impaired IL-4 induced lymphocyte proliferation, an impaired IgE response, and an impaired Th2 cell response.

2. A method for determining the effect of a candidate drug on a mouse deficient in Stat6 function, said method comprising the steps of:

contacting a transgenic mouse according to claim 1 with a candidate drug; and detecting the presence or absence of a physiological change in said mouse in response to said contacting step.

* * * * *